United States Patent
Ludescher et al.

(10) Patent No.: US 6,333,409 B1
(45) Date of Patent: Dec. 25, 2001

(54) PROCESS FOR THE PURIFICATION OF A 3-CEPHEM-4-CARBOXYLIC ACID DERIVATIVE

(75) Inventors: Johannes Ludescher, Breitenbach; Bernhard Prager, Wörgl; Siegfried Wolf, Brixlegg, all of (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 09/564,833

(22) Filed: May 4, 2000

Related U.S. Application Data

(62) Division of application No. 09/190,200, filed on Nov. 12, 1998, now Pat. No. 6,136,967, which is a division of application No. 08/466,306, filed on Jun. 6, 1995, now Pat. No. 5,869,648, which is a continuation of application No. 08/284,515, filed as application No. PCT/EP92/02965 on Dec. 21, 1992, now abandoned.

(30) Foreign Application Priority Data

Feb. 5, 1992 (AT) ........................................ 191/92
Dec. 9, 1992 (GB) .................................... 9225666

(51) Int. Cl.⁷ ..................... C07D 501/06; C07D 501/22
(52) U.S. Cl. ............................. 540/215; 540/222
(58) Field of Search .................... 540/215, 222

(56) References Cited

U.S. PATENT DOCUMENTS

| | | | |
|---|---|---|---|
| 3,769,277 | 10/1973 | Long et al. | 260/243 C |
| 4,065,620 | 12/1977 | Webb | 260/243 C |
| 4,107,431 | 8/1978 | Clark et al. | 544/16 |
| 4,110,534 | 8/1978 | Clark et al. | 544/16 |
| 4,520,022 | 5/1985 | Hoshi et al. | 514/200 |
| 4,694,079 | 9/1987 | Crast, Jr. | 540/215 |
| 4,727,070 | 2/1988 | Kaplan et al. | 514/202 |
| 4,847,373 | 7/1989 | Baker et al. | 540/215 |
| 5,132,419 | 7/1992 | Lanz et al. | 540/215 |

FOREIGN PATENT DOCUMENTS

| | | |
|---|---|---|
| 0292806 | 11/1988 | (EP) . |
| 0304036 | 2/1989 | (EP) . |
| 0355821 | 2/1990 | (EP) . |
| 0421219 | 4/1991 | (EP) . |
| 0472060 | 2/1992 | (EP) . |
| 0503453 | 9/1992 | (EP) . |
| 2540117 | 8/1984 | (FR) . |
| 2173798A | 10/1986 | (GB) . |
| 2178032 | 2/1987 | (GB) . |

OTHER PUBLICATIONS

House, H. O. et al., "The Chemistry of Carbanions. VI. Stereochemistry of the Wittig Reaction with Stabilized Ylids", J. Org. Chem., vol. 29, (1964), pp. 3327–3333.

Kamachi et al., "Improved Synthesis of an Ester–Type Prodrug, 1–acetoxyetyyl 7–[(Z)]–2–(2–aminothiazol–4–yl)–2–hydroxyiminoacetamido–3–[(Z)]–1–Propenyl–3–Cephem–4–Carboxylate (BMY–28271)", The Journal of Antibiotics, Dec. 1990, pp. 1564–1572.

Pharmacopeial Forum—vol. 18, No. 4, Jul.–Aug. 1992, pp. 3635–3637.

*Primary Examiner*—Mark L. Berch
(74) *Attorney, Agent, or Firm*—Lydia T. McNally

(57) ABSTRACT

The invention relates to a new process for the depletion of 7-amino-3-[(E)-1-propen-1-yl]-3-cephem-4-carboxylic acid in mixtures of 7-amino-3-[(Z)-1-propen-1-yl]-3-cephem-4-carboxylic acid and 7-amino-3-[(E)-1-propen-1-yl]-3-cephem-4-carboxylic acid, by means of the crystalline hydrochloride or a metal or amine salt of 7-amino-3-[(z/E)-1-propen-1-yl]-3-cephem-4-carboxylic acid or by adsorption chromatography.

11 Claims, No Drawings

PROCESS FOR THE PURIFICATION OF A 3-CEPHEM-4-CARBOXYLIC ACID DERIVATIVE

This application is a divisional of U.S. application Ser. No. 09/190,200, filed Nov. 12, 1998, U.S. Pat. No. 6,136,967 which is a divisional of U.S. application Ser. No. 08/466,306, filed Jun. 6, 1995, now U.S. Pat. No. 5,869,648, which is a continuation of U.S. application Ser. No. 08/284,515, filed Aug. 5, 1994 now abandoned, which is a 371 of application PCT/EP92/02965, filed Dec. 21, 1992.

Process for the purification of a 3-cephem-4-carboxylic acid derivative

The invention relates to methods of reducing the E-(trans) isomer amount in the Z/E (cis/trans) 7-amino-3-(1-propen-cephem-4-carboxylic acid of formula I

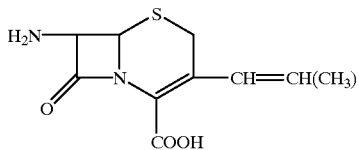

The Z-isomer, 7-amino-3-[(Z)-1-propen-1-yl]-3-cephem-4-carboxylic acid of formula Ia

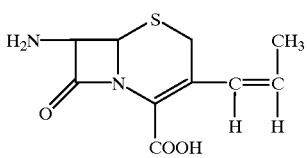

is a central intermediate for the production of highly effective broad-band antibiotics, for example cefprozil and BAY v 3522 of formulae

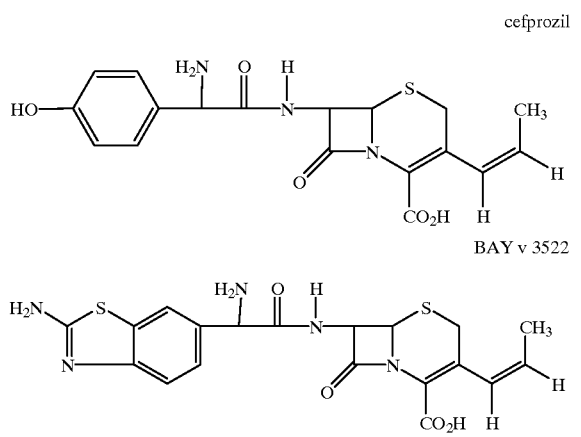

It is known that the Z-(or cis-)configuration represents the characteristic which determines the advantageous antibacterial properties of cephalosporin end products in the Gram negative range. Consequently, an active substance with the smallest possible proportion of E-(or trans-) isomer is desired for optimum efficiency. For example the undesired E-isomer in cefprozil should not exceed 11% according to the US Pharmocopeia.

Synthetic processes for the production of these antibiotics generally yield Z-isomers in admixture with E-isomers.

During the synthesis of the double bond from the corresponding cephalosporin nucleus by means of a Wittig reaction with acetaldehyde, the ratio of Z- to E-isomers may only be guided in the desired direction to an unsatisfactory extent : UK Patent Application 2 135 305 describes the production of cefprozil, starting with 7β-[D-2-(t-butoxycarbonylamino)-2-(p-hydroxyphenyl)acetamido]-3-cephem-4-carboxylic acid benzhydrylester. In Procedure-8 of this UK Application, the trans-isomer is separated by high performance liquid chromatography.

In U.S. Pat. No. 4,727 070, a Z/E mixture of 7-[D-2-amino-2-(Z-and E)-1-propen-1-yl)ceph-3-em-4-carboxylic acid (cefprozil) is freed from undesired E isomer by means of a reaction with acetone and subsequent re-cleavage to the active substance. Purification of a most advanced intermediate by chromatography is expensive, and purification by chemical derivation of the end product is of course the most expensive variant.

Less expensive is the production of the relatively isomer-free intermediate product, namely 7-amino-3-[(Z)-1-propen-1-yl]-3-cephem-4-carboxylic acid. However, the necessary olefinization reaction may not progress sufficiently selectively to the desired Z-compound. For example, in UK Patent Application 2 173 798, 7-amino-3-(1-propen-1-yl)-3-cephem-4-carboxylic acid benzhydryl ester.hydrochloride is obtained for example as a maximum 90/10 Z/E mixture in a Wittig reaction as an intermediate stage to the antibiotic cefprozil. From this, ester cleavage takes place to produce 7-amino-3-[(Z)-1-propen-1-yl]-3-cephem-4-carboxylic acid with a proportion of Z-isomer of 9.7%. In Example 4, the ratio of Z/E is 83/17. In EP-A-O 292 806, 7-amino-3-(1-propen-1-yl)-3-cephem-4-carboxylic acid is produced with a maximum Z/E ratio of 91/9. Further purification at the stage of this central intermediate product is not described.

It has been surprisingly found that Z/E 7-amino-3-(1-propen-1-yl]-3-cephem-4-carboxylic acid of formula I with a too high E proportion may be converted into compound of formula I with low E content via the hydrochloride, a metal or amine salt of the compound of formula I or by adsorption chromatography of the compound of formula I.

In particular the invention comprises simple and efficient methods of depleting 7-amino-3-[(E)-1-propen-1-yl]-3-cephem-4-carboxylic acid in Z/E mixtures of 7-amino-3-[1-propen-1-yl]-3-cephem-4-carboxylic acid by a) forming the hydrochloride of the compound of formula I'

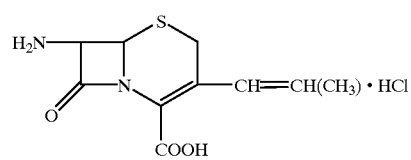

wherein the propenyl group has Z- and E-configuration, from compound of formula I and hydrochloric acid in a solvent or solvent mixture, in which the Z- and E-isomers of formula I' have different solubilities or solubilising at least part of 7-amino-3-[(E)-1-propen-1-yl]-3-cephem-4-carboxylic acid hydrochloride in Z/E mixtures of the compound of formula I' in a solvent or solvent mixture, in which the Z- and E-isomers have different solubilities, and recovering the enriched Z-isomer of formula I', and optionally converting the obtained compound of formula I' into the free compound of formula I with a reduced E-amount by adjusting the pH or b) forming a salt of formula II

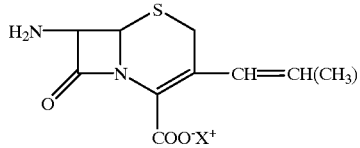

wherein the propenyl group has Z- and E-configuration and X⁺ is Li⁺, Na⁺, K⁺, ammonium or a cation of formula III

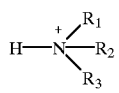

wherein $R_1$, $R_2$ and $R_3$ are independently hydrogen, ($C_{1-8}$)alkyl, an optionally substituted benzyl, ($C_{4-8}$) cycloalkyl or $R_1$ with $R_2$ and the nitrogen atom signify a 5- or 6-membered heterocycle which optionally contains one or two additional heteroatoms and $R_3$ is as defined above, whereby one of $R_1$, $R_2$ or $R_3$ is not hydrogen, by reacting a compound of formula I with a lithium, sodium or potassium base or ammonia or an amine of formula IV

wherein $R_1$, $R_2$ and $R_3$ are as defined above, in a solvent or solvent mixture, in which the Z- and E-isomers of formula II have different solubilities and precipitating the obtained compound of formula II optionally by adding a counter solvent, or dissolving a compound of formula I in a solvent or solvent mixture with a lithium, sodium or potassium base or ammonia and precipitating a compound of formula II by adding a lithium, sodium or potassium source or an amine of formula IV and optionally a counter solvent, and converting the compound of formula II into compound of formula I with a reduced E-amount or the hydrochloride thereof of formula I' by adding an acid, or c) subjecting a solution of the compound of formula I to adsorption chromatography.

Process a) may be carried out as follows:

The formation of the hydrochloride is carried out in a solvent or solvent mixture, in which the Z- and E-isomers of formula I' have different solubilities.

The hydrochloride of formula I' may be formed both in protic and in aprotic medium. If operating in an aqueous system, the Z/E mixture of the compound of formula I is dissolved in water or an aqueous organic solvent such as aqueous alcohol, e.g. isopropanol, aqueous acetone or acetonitrile, by adding hydrochloric acid, and precipitating the hydrochloride by addition of an organic counter solvent.

Suitable organic counter solvents are in particular organic nitriles such as acetonitrile; ketones, e.g. acetone; alcohols, e.g. methanol, ethanol, one of the isomeric propanols or butanols; ethers, e.g. tert.butyl methyl ether, diethylether or tetrahydrofuran or esters, e.g. ethyl or isopropyl acetate or mixtures thereof. If operating in a practically water-free system, the Z/E mixture of formula I is dissolved in concentrated form in an alcohol, e.g. methanol or isopropanol, with water-free hydrochloric acid, and is then diluted with one of the above mentioned counter solvents, whereby the crystalline Z-enriched product is crystallized out.

According to another variant, the hydrochloride of formula I' may be suspended or dissolved in a solvent or solvent mixture in which the E-isomer of 7-amino-3-(1-propen-1-yl)-3-cephem-4-carboxylic acid hydrochloride is better soluble than the corresponding Z-isomer. Suitable solvents are alcohols, e.g. methanol, ethanol or isopropanol or a sulfone, e.g. sulfolane. Precipitation is then induced by e.g. adjustment of the solubility product of the Z- or E-isomer optionally by addition of one of the above mentioned counter solvent, whereby the hydrochloride of compound of formula I, with a reduced E-amount is obtained.

The hydrochloride which is thereby much improved in its Z/E ratio may subsequently be converted again into the compound of formula I in conventional manner, e.g. by means of pH adjustment in water to the approximate isoelectric point.

If a mixture of Z and E 7-amino-3-(1-propen-1-yl)-3-cephem-4-carboxylic acid of formula I is dissolved in water in an alkali or an acid and is then reprecipitated by setting the pH at the isoelectric point, there is no improvement, but rather a worsening of the Z/E ratio (see comparison tests in Examples 11a and 11b). On the other hand, using the crystalline hydrochloride of 7-amino-3-(1-propen-1-yl)-3-cephem-4-carboxylic acid of formula I', the Z/E ratio is surprisingly considerably improved. The depletion rates of undesired E-compound are up to 7%.

Compounds of formula I' may be prepared as described by the processes herein containing various amounts of Z/E isomers, e.g. in a ratio of 91:9 or less, 92:8 or less, conveniently 94:6 or more, or 95:5 or less; 97:3 or less; 99:1 or less.

The crystalline hydrochloride of formula I' is new and also form part of the invention. The hydrochloride of formula I' having a Z/E ratio of at least 91:9 or less is also new and form part of the invention.

Process b) may be effected as follows:

The compounds of formula II may be formed in a protic or in an aprotic medium. If operating in an aqueous system, the Z/E mixture of the compound of formula I is dissolved in water or an aqueous organic solvent auch as acetone or an alcohol e.g. isopropanol, by adding a base, such as lithium, sodium or potassium base, e.g. hydroxide, carbonate or hydrogencarbonate or a nitrogen containing base such as ammonia. Then an amine of formula IV or a lithium, sodium or potassium source is added and the solution optionally diluted with an organic counter solvent, whereby a compound of formula II precipitates. Alternatively the Z/E mixture of the compound of formula I may be suspended in water, or an aqueous organic solvent such as acetone or an alcohol, e.g. isopropanol, the suspension is treated first with a lithium, sodium or potassium source or ammonia or a compound of formula IV and then with an organic counter solvent and optionally adjusting the pH with lithium, natrium or potassium base, e.g. hydroxide, carbonate or bicarbonate in case a lithium, sodium or potassium source such as lithium, sodium or potassium acetate is used.

Examples of organic counter solvents are given in process a) above.

Typical lithium, sodium or potassium sources include lithium, sodium or potassium salts of carboxylic acids, such as sodium or potassium acetate or lithium, sodium or potassium 2-ethylhexanoate.

If operating in an aprotic medium, the Z/E mixture of formula I is suspended in an organic solvent, adding a base of formula IV and optionally diluting with a counter solvent or a mixture of counter solvents. Examples of organic solvents are amides, e.g. dimethylformamide; sulfoxide, e.g. dimethylsulfoxide; sulfone, e.g. sulfolane; halogenated hydrocarbons, e.g. dichloromethane; ketones, e.g. acetone; esters; ethers, e.g. tetrahydrofuran; alcohols, e.g. methanol, ethanol, one of the isomeric propanols or butanols, nitrites e.g. acetonitrile or mixtures of these solvents. Further solvents may be added in admixture such as diethyl ether or tert. butyl methyl ether. Examples of compounds of formula IV are tert.butylamine, benzylamine, dibenzylamine, dicyclohexylamine or 2,4,4-trimethylpentyl-2-amine.

If in compounds of formula IV $R_1$ with $R_2$ and the nitrogen atom signify a 5- or 6-membered heterocycle, containing optionally 1 or 2 additional heteroatoms, these are preferably oxygen or sulphur atoms. Examples of the heterocycle are morpholine, N-methyl-morpholine, oxazolidine or thiazolidine.

Preferred examples of compounds of formula IV are dicyclohexylamine and 2,4,4-trimethylpentyl-2-amine.

The compounds of formula II may be easily converted into compounds of formula I with a reduced E content, by dissolving or suspending a compound of formula II in water and by acidifying, whereby the nitrogen containing base may optionally be removed by extraction in a first alkaline step or kept in solution by addition of an organic solvent such as an alcohol or a ketone, when the base is forming a salt, which is poorly soluble in water.

Alternatively compounds of formula II may be converted into compound I'.

Compounds of formula II, wherein $X^+$ is ammonium or a cation of formula III are new and also form part of the invention. The dicyclohexylammonium salt and the (2,4,4-trimethylpentyl-2) ammonium salt are preferred.

Process b) has several advantages. Compounds of formula II are easily precipitated and crystallized. Process b) is especially advantageous, when applied to Z/E mixtures of formula I with a high E-content and/or containing by-products e.g. those obtained from mother liquors, e.g. from process a) or early eluting fractions from process c) containing by-products, effording products with a low E-content and high purity (see Example 4b). The fact that the process is applicable to products derived from mother liquors has also the advantage of an improved total yield.

Processes a) and b) may be optionally repeated or compounds of formula II may be converted-into the compound of formula I' in order to obtain the desired Z/E ratio.

Process c) may be carried out as follows:
The compound of formula I is dissolved in water by adding a base e.g. ammonia. Adsorbents include activated carbon, e.g. Norit CG-1, SX-plus, C-granular or Cecarbon GAC 40; adsorption resins such as HP-20, HP-21 or SP 207 (from e.g. Mitsubishi); XAD-1180, XAD-1600 or XAD 16 (from e.g. Rohm-Haas) or Amberchrome CG 161 (from e.g. Toso-Haas). Preferably the adsorption resin is XAD-1600 or Amberchrome CG 161. Elution is effected with water. In this process the E-isomer has a better adsorption than the Z-isomer and thus is slower eluted as the Z-isomer. The first eluted fractions contain therefore mainly the Z-isomer, whereas the latest fractions contain mainly the E-isomer. The desired product may then be obtained by adjusting the pH value close to the isoelectric point, i.e. to 2.5–4.5, preferably to 3.0–3.7, whereby crystallization occurs. Depending on which fractions are combined, products with a very low amount of E-isomer (<3%) or products with an E-isomer of 7–9% are obtained.

The amount of the adsorbent depends on the desired dissolution rate and the Z/E ratio of the starting compound of formula I.

Process c) represents a very simple and economical method. The adsorbents may be regenerated. The elution is effected with water, no organic eluants are used. The apparative equipment is simple. No gradient elution or stepwise elution and no changes of pH are necessary.

Processes a), b) and c) are suitable for industrial scale.

In the following Examples, which illustrate the invention more fully, but in no way limit its scope, all temperatures are given in degrees celsius.

In the Examples the following abbreviations are used:
PACA=7-amino-3-[(Z/E)-1-propen-1-yl]-3-cephem-4-carboxylic acid 7-ACA=7-amino-cephalosporanic acid 7-ADCA=7-amino-desacetoxy-cephalosporanic acid.

1. Production of E-depleted 7-amino-3-[(Z/E)-1-propen-1-yl]-3-cephem-4-carboxylic acid.hydrochloride [process a]

EXAMPLE 1a

A mixture of 15 ml of 5 N HCl in methanol and 30 ml of acetonitrile is cooled with ice water. 15 g of PACA (Z/E ratio=85.4/14.6) are introduced into the solution. After stirring for 5 minutes, a solution is obtained. The cooling bath is removed and the solution is slowly diluted over the course of 30 minutes with the dropwise addition of 300 ml of acetonitrile. After adding ca. 70 ml of acetonitrile, the solution is seeded with PACA.hydrochloride. The resultant crystal suspension is stirred for a further one hour whilst cooling with ice. The product is isolated through a suction filter, washed twice, each time with 40 ml of acetonitrile, and dried in a vacuum drying chamber.

| | |
|---|---|
| Yield: | 14.1 g |
| Chloride: | 12.8% |
| Z/E ratio: | 89.9/10.1 |

EXAMPLE 1b 10 ml of acetonitrile and 5 ml of aqueous concentrated HCl are cooled with ice water, and 5 g of PACA with a Z/E ratio of 85.4/14.6 are introduced whilst stirring. After ca. 20 minutes, a solution is obtained. The solution is slowly mixed with 100 ml of acetonitrile, whereby after the addition of 30 ml of the acetonitrile, the solution is seeded with the hydrochloride of PACA. After completion of the acetonitrile addition, the resultant crystal suspension is stirred for a further one hour whilst cooling with ice, and subsequently filtered. The hydrochloride is subsequently washed twice, each time with 15 ml of acetonitrile, and dried.

| Yield:    | 3.4 g    |
|-----------|----------|
| Z/E ratio:| 92.8/7.2 |

EXAMPLE 1c 1 g of PACA.hydrochloride with a Z/E ratio of 89.1/10.1 is treated with 2 ml of methanol, whereby a solution is briefly obtained. Crystallization rapidly re-occurs. The suspension is slowly mixed with 20 ml of acetonitrile. The crystal suspension is stirred for a further 1 hour whilst cooling with ice, and subsequently filtered. The product is washed twice, each time with 5 ml of acetonitrile, and dried.

| Yield:    | 0.6. g   |
|-----------|----------|
| Z/E ratio:| 95.5/4.5 |

EXAMPLE 1d 1 g of PACA.hydrochloride with a Z/E ratio of 89.9/10.1 is suspended per 2 ml of methanol, ethanol and isopropanol. After stirring for one hour and cooling with ice, the solid substance is isolated in the usual way, and dried.

|                | Z/E ratio: |
|----------------|------------|
| a) methanol    | 97.2/2.8   |
| b) ethanol     | 91.1/8.9   |
| c) isopropanol | 92.5/7.5   |

2. Conversion of 7-amino-3-[(Z/E)-1-propen-1-yl]-3-cephem-4-carboxylic acid.hydrochloride into 7-amino-3-[(Z/E)-1-propen-1-yl]-3-cephem-4-carboxylic acid

EXAMPLE 2

2 g of PACA.hydrochloride with a Z/E ratio of 89.9/10.1 are introduced into 20 ml of water. The pH value of the suspension is 0.9. The suspension is carefully adjusted to pH 3.5 with 2 N NaOH. The suspension is stirred for a further 1 hour whilst cooling with ice, the product is filtered off, washed twice, each time with 5 ml of water, and dried.

| Yield:    | 1.7 g     |
|-----------|-----------|
| Z/E ratio:| 89.7/10.3 |

3. Production of E-depleted 7-amino-3-[(Z/E)-1-propen-1-yl]-3-cephem-4-carboxylic acid potassium salt [process (b)]

EXAMPLE 3

To a mixture of 20 ml saturated aqueous potassium acetate solution and 20 ml isopropanol are added 10 g of PACA (mother liquor product) (Z/E ratio=63:37) with a content of 90% (main side product 7-ADCA 1.9%). The pH of the obtained suspension is adjusted with SN KOH to pH 8.8 and the resulting solution is diluted with 100 ml isopropanol. The resulting suspension is stirred 1 hour at room temperature and then left overnight in the refrigerator. The precipitate is filtered off, washed with isopropanol and dried.

| Yield:             | 5.1 g              |
|--------------------|--------------------|
| Content PACA (HPLC):| 86% = 99.7% as potassium salt; |
| Z/E ratio:         | 70.8/29.2          |
| Content 7-ADCA:    | 0.4%               |

4. Production of E-depleted 7-amino-3-[(Z/E)-1-propen-1-yl]-3-cephem-4-carboxylic acid dicyclohexylammonium salt [process b)]

EXAMPLE 4a 10 g of PACA (Z/E ratio 92/8) (HPLC content 99%) are suspended in a mixture of 30 ml water and 30 ml acetone. Aqueous ammonia is added until a solution results. The basic solution (pH ca 8.8) is treated with 9.1 ml dicyclohexylamine and then dropwise with 250 ml acetone, whereby PACA-dicyclohexyl-ammonium salt precipitates. The suspension is stirred for a further 1 hour at room temperature and the product is filtered off, washed with acetone and dried in a vacuum chamber.

| Yield:                        | 13.5 g |
|-------------------------------|--------|
| Content PACA (HPLC):          | 53.3%  |
| Content Dicyclohexylamine (GC):| 39.3%  |
| Content water:                | 1.7%   |
| Content acetone:              | 1.1%   |
| Z/E ratio:                    | 96/4   |

EXAMPLE 4b 200 g of PACA (mother liquor product) with a Z/E ratio of 56.4/43.6 (HPLC content 90.1%, 3.2% 7-ADCA, 1.6% 7-ACA) are suspended in a mixture of 1600 ml acetone and 400 ml water. Under stirring are added 182.4 ml of dicyclohexylamine, whereby a solution results after a few minutes. Seed crystalls of PACA dicyclohexylammonium salt are added and the resulting suspension is stirred 2 hours at room temperature. The suspension is left in a refrigerator overnight, the product is filtered off, washed with acetone and dried in a vacuum chamber at 45°.

| Yield:              | 200.2 g   |
|---------------------|-----------|
| Z/E ratio:          | 78.3/21.7 |
| Content PACA (HPLC):| 48%       |
| Content 7-ADCA:     | 0.22%     |
| Content 7-ACA:      | 0.19%     |

EXAMPLE 4c

A suspension of 10 g of PACA with a Z/E ratio of 86/14 (HPLC content 93.4%) in 50 ml dichloromethane is treated with 12.4 ml of dicyclohexylamine, whereby a slightly clouded solution results. Crystallisation is starting and the suspension is cooled, the product filtered off, washed with cold dichloromethane and dried in a vacuum chamber.

| | |
|---|---|
| Yield: | 11.2 g |
| PACA content (HPLC): | 56.2% |
| Z/E ratio: | 90.2/9.8 |

5. Production of E-depleted 7-amino-3-[(Z/E)-1-propen-1-yl]-3-cephem-4-carboxylic acid tert. octylammonium salt [process b)]

EXAMPLE 5

A suspension of 10 g PACA with a Z/E ratio 86.3/13.7 (HPLC content 95%) in a mixture of 80 ml acetone and 40 ml water is treated with 7.6 ml tert.-octylamine. Further 520 ml of acetone are added. The obtained suspension is stirred for 2 hours at room temperature. The tert. octylammonium [(2,4,4-trimethylpentyl-2) ammonium] salt of PACA is filtered off, washed with acetone and dried in a vacuum chamber.

| | |
|---|---|
| Yield: | 10.4 g |
| PACA content (HPLC): | 59.8% |
| Z/E ratio: | 92.5/7.5 |
| Content tert. octylamine (GC): | 31.6 |
| $H_2O$: | 1.6% |
| Acetone (GC): | 2% |

6. Production of 7-amino-3-[(Z/E)-1-propen-1-yl]-3-cephem-4-carboxylic acid from 7-amino-3-[(Z/E)-1-propen-1-yl]-3-cephem-4-carboxylic acid dicyclohexylammonium salt

EXAMPLE 6a 100 g PACA-dicyclohexylammonium salt [product of Example 4b)] with a Z/E ratio of 78.3/21.7 (HPLC content 48% of PACA) are suspended in 1000 ml water. The pH of the suspension is adjusted to pH 3.5 within 45 minutes with 85% phosphoric acid. The suspension is stirred for a further 30 minutes at room temperature. The title product is filtered off, washed with water and then with acetone and dried in a vacuum chamber.

| | |
|---|---|
| Yield: | 45.7 g |
| Content HPLC: | 100.8% |
| Z/E ratio: | 77.8/22.2 |

EXAMPLE 6b 100 g PACA-dicyclohexylammonium salt (E-content 7.6%, PACA-content 53.11%) are added to 4000 ml water of 300. After about 2 minutes a solution results, to which 5 g activated carbon are added. The mixture is stirred for 10 minutes, the carbon is filtered off and washed with 250 ml water. The pH of the combined filtrate and washing is slowly adjusted to 3.5 with 5 N sulfuric acid. The obtained crystal suspension is cooled in an ice-bath and stirred for 2 hours while cooling. The product is filtered off, washed sequentially with total 200 ml water, 100 ml water/acetone (1:1) and 250 ml acetone. The product is dried in a vacuum chamber at 40°.

| | |
|---|---|
| Yield: | 50.3 g |
| Content HPLC: | 101.5% |
| E-content: | 7.4% |

7. Production of E-depleted 7-amino-3-[(Z/E)-1-propen-1-yl]-3-cephem-4-carboxylic acid [process c)]

EXAMPLE 7

7.8 liters of aqueous solution of 2 kg PACA (content 93.4%, E content 15%), obtained by addition of ammonia up to a pH of 8.0, are loaded on a 75 liter column filled with HP-20-resin with a flow rate of 60 liter/h. The elution is effected with water. 50 liters of eluate (counting from the beginning of the introduction of the PACA-solution) are obtained. This does not contain the product (HPLC control) and is discarded. Then fractions each of 5 l are taken and analysed by HPLC. The first 2 fractions contain a small amount of Z-PACA, but also early eluting side products such as 7-ACA and 7-ADCA and are combined to Pool I. The subsequent 6 fractions ($\epsilon$=30 liters) contain mainly the desired Z-PACA (1108 g Z-PACA+27 g E-PACA).

The following 7 fractions ($\epsilon$=35 liters) contain still Z-PACA, but also increasing amounts of E-PACA (297 g Z and 93 g E). From the HPLC analysis of these 13 fractions the E-content is calculated of 7.9%. These 13 fractions are combined and the pH is adjusted to 3.5 by addition of SN HC1. The precipitating crystalls are filtered off, washed with water and acetone and dried in vacuum at 45°. There are obtained 1451 g PACA (yield 77.6%).

| | |
|---|---|
| Content PACA: | 99.9% |
| E-content: | 7.8% |

From Pool I there are obtained by adjusting the pH to 3.5 137.5 g material, which consists mainly of Z-PACA.

Out of later eluting fractions (fractions 16–19) 62.4 g of mainly E-PACA are isolated by adjusting the pH to 3.5.

EXAMPLE 8

20 g activated carbon (Norit CG-1) are suspended in water and then filtered on a suction filter (diameter 4 cm) and rinsed in vacuum with water. 4 g PACA (content 93.4%, E-content 15%) are dissolved in 40 ml water by addition of ammonia up to a pH of 8.0. This solution is slowly sucked (within ca. 15 minutes through the activated carbon. Afterwards the carbon-cake is eluted in the same manner with 250 ml water.

The filtrates are collected in fractions of each about 40 ml. The first 2 fractions do not contain the product (HPLC control). Fractions 3 to inclusive 7 contain mainly the Z-PACA and only a very small amount of E-PACA and are therefore combined. These 230 ml are adjusted with 2N HCl to pH 3.4, whereby the product crystallises. The product is filtered off, washed with water and acetone and dried to yield 2.8 g PACA (content 96.7%) and containing <0.1% E isomer.

| Yield: | 72.5% |
|---|---|

EXAMPLE 9

100 ml adsorbent-resin "Amberchrome CG 161 md" are loaded as in Example 7 described with a solution of 5 g PACA (content 93.4%, E-content 15%) in 50 ml water. Elution is then effected with water and the eluates containing Z-PACA fractions are collected. Adjustment of the pH to 3.5 leads to crystallisation of the product, which is filtered, washed and dried, to give 3.87 g (yield 82.8%) PACA (content 98%) and containing <5% E isomer.

The resin is regenerated by elution with aqueous isopropanol to which some ammonia is added., rinsed with water and may be again employed.

EXAMPLE 10

To the regenerated resin "Amberchrome CG 161 md" of Example 9 (100 ml volume) is introduced an aqueous solution of 8 g PACA (content 93.4%, E-content 15%)- prepared by dissolving with ammonia solution at pH 8.1 in 60 ml water. Elution with 240 ml water is then effected. 110 ml of "empty" eluate and further 10 ml eluate, containing mainly early eluting side products such as 7-ACA, 7-ADCA etc. are discarded. Thereafter the eluate is pooled until the E-content in the pool is increased up to 9% E-PACA related to the total amount of PACA in the pool. From this pool (200 ml) the product is crystallised by adjusting the pH to 3.4 with hydrochloric acid. The product is filtered, washed with water and dried in vacuum. 6.4 g PACA (yield 85.6%, content 99%) with an E-content of 8.8% are obtained.

The adsorption resin is thereafter regenerated as described in Example 9.

11. Comparison tests for depletion, by dissolving and reprecipitating 7-amino-3-(1-propen-1-yl)-3-cephem-4-carboxylic acid

EXAMPLE 11a 3 g of PACA with a Z/E ratio of 85.4/14.6 are suspended in 30 ml of water. Ca. 6 ml of concentrated HCl are added whilst cooling with ice, until a solution is obtained. The pH value is subsequently adjusted to pH 3.5 by carefully adding 5 N NaOH without external cooling. The crystal suspension is then stirred for 1 hour whilst cooling with ice, the product is filtered off, washed twice, each time with 10 ml of water, and dried in a vacuum drying chamber.

| Yield: | 2.8 g |
|---|---|
| Z/E ratio: | 84.5/15.5 |

EXAMPLE 11b 3 g of PACA with a Z/E ratio of 82.6/17.6 are suspended in 50 ml of water. 5 N NaOH (ca. 2.5 ml) is added whilst stirring until a solution is obtained (pH 8.7). The pH is subsequently adjusted to pH 3.5 by carefully adding concentrated HCl, diluted to 1/1. The crystal suspension is stirred for a further 1 hour whilst cooling with ice, and subsequently isolated and dried as described in Example 3a).

| Yield: | 2.9 g |
|---|---|
| Z/E ratio: | 81.8/18.2 |

What is claimed is:
1. A process for the production of a highly effective broad-band antibiotic comprising the steps of
   i) preparing a (Z)-isomer enriched 7-amino-3-(1-propen-1-yl)-3-cephem4-carboxylic acid in free acid or salt form by depleting 7-amino-3-{(E)-1-propen-1-yl}-3-cephem-4-carboxylic acid in a mixture of 7-amino-3-{(Z)-1-propen-1-yl}-3-cephem4-carboxylic acid and 7-amino-3-{(E)-1-propen-1-yl}-3-cephem-4-carboxylic acid by reacting a mixture of the (Z)- and (E)-isomers of the compound of the formula

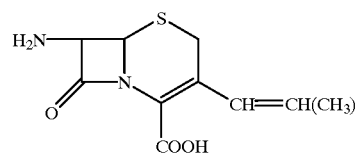

I with hydrochloric acid, a lithium, sodium or potassium base, ammonia, or an amine of formula IV to form a salt of formula I

IV wherein $R_1$, $R_2$ and $R_3$ are independently hydrogen, $(C_{1-8})$alkyl, benzyl, $(C_{4-8})$cycloalkyl; or
$R_1$ with $R_2$ and the nitrogen atom together form a 5- or 6-membered heterocycle which may contain one or two additional heteroatoms and $R_3$ is as defined above, wherein one of $R_1$,
$R_2$ and $R_3$ is other than hydrogen; in a solvent or solvent mixture in which the Z- and E-isomers of said salt of formula I have different solubilities and where the E isomer is better soluble than the Z isomer and if desired, isolating a (Z)- isomer enriched 7-amino-3-(1-propen-1-yl)-3-cephem-4-carboxylic acid in free acid or salt form obtained by recovering said salt of (Z)- isomer enriched 7-amino-3-(1-propen-1-yl)-3-cephem-4-carboxylic acid after precipitation and where required, converting the enriched (Z)-isomer of the salt of formula I into the free acid of formula I; and
   ii) further acylating said (Z)-isomer enriched 7-amino-3-(1-propen-1-yl)-3-cephem-4-carboxylic acid in free acid or salt form at the amine group in position 7 to obtain a highly effective broad-band antibiotic.
2. A process according to claim 1 wherein the compound of formula I is reacted with hydrochloric acid.
3. A process according to claim 1 wherein the compound of formula I is reacted with hydrochloric acid to give a mixture of 7-amino-3-{(Z)-1-propen-1-yl}3-cephem4- carboxylic acid hydrochloride and 7-amino-3{(E)-1-propen-1-yl}3-cephem4-carboxylic acid hydrochloride having a Z/E ratio of 91:9 to 99:1.

4. A process according to claim 1 wherein a Z-isomer enriched 7-amino-3-(1-propen-1-yl)-3-cephem-4-carboxylic acid in free acid or salt form obtained in step i) is acylated at the amine group in position 7 of the ring system.

5. A process according to claim 1 wherein the highly effective broad band antibiotic is cefprozil having the formula

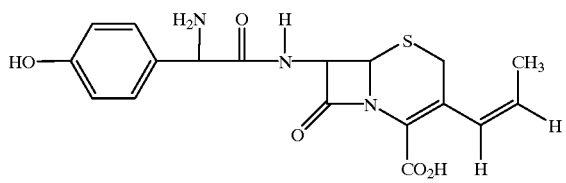

or has the formula

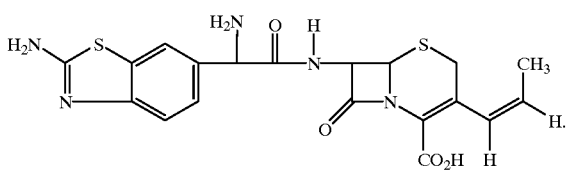

6. A process for the production of a pharmaceutically effective cephalosporin comprising the steps of
i) preparing a (Z)-isomer enriched 7-amino-3-(1-propen-1-yl)-3-cephem-4-carboxylic acid in free acid or salt form by depleting 7-amino-3{(E)-1-propen-1-yl}-3-cephem4-carboxylic acid in a mixture of 7-amino-3-{(Z)-1-propen-1-yl}-3-cephem4-carboxylic acid and 7-amino-3-{(E)-1-propen-1-yl}-3-cephem-4-carboxylic acid by reacting a mixture of the (Z)- and (E)-isomers of the compound of formula

I

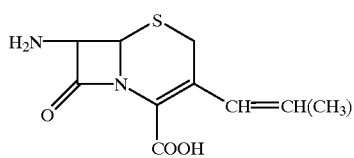

with hydrochloric acid, a lithium, sodium or potassium base, ammonia, or an amine of formula IV to form a salt of formula I

IV

wherein $R_1$, $R_2$ and $R_3$ are independently hydrogen, $(C_{1-8})$alkyl, benzyl, $(C_{4-8})$cycloalkyl; or
$R_1$ with $R_2$ and the nitrogen atom together form a 5 or 6-membered heterocycle which may contain one or two additional heteroatoms and $R_3$ is as defined above, wherein one of $R_1$,
$R_2$ and $R_3$ is other than hydrogen; in a solvent or solvent mixture in which the Z- and E-isomers of said salt of formula I have different solubilities and where the E isomer is better soluble than the Z isomer and if desired, isolating a (Z)- isomer enriched 7-amino-3-(1-propen-1-yl)-3-cephem-4-carboxylic acid in free acid or salt form obtained by recovering said salt of (Z)- isomer enriched 7-amino-3-(1-propen-1-yl)-3-cephem4-carboxylic acid after precipitation and where required, converting the enriched (Z)-isomer of the salt of formula I into the free acid of formula I; and ii) further acylating said (Z)-isomer enriched 7-amino-3-(1-propen-1-yl)-3-cephem4-carboxylic acid in free acid or salt form at the amine group in position 7 to obtain a pharmaceutically active cephalosporin antibiotic.

7. A process according to claim 6 wherein the compound of formula I is reacted with hydrochloric acid.

8. A process according to claim 6 wherein the compound of formula I is reacted with hydrochloric acid to give a mixture of 7-amino-3-{(Z)-1-propen-1-yl}-3-cephem-4-carboxylic acid hydrochloride and 7-amino-3-{(E)-1-propen-1-yl}-3-cephem4-carboxylic acid hydrochloride having a Z/E ratio of 91:9 to 99:1.

9. A process according to claim 6 wherein a Z-isomer enriched 7-amino-3-(1-propen-1-yl)-3-cephem-4-carboxylic acid in free acid or salt form obtained in step i) is acylated at the amine group in position 7 of the ring system.

10. A process according to claim 6 wherein the pharmaceutically effective cephalosporin is cefprozil having the formula

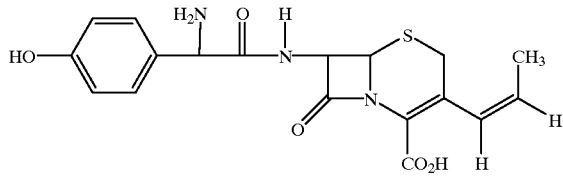

or

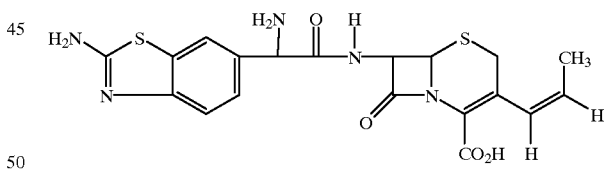

11. A process for the production of cefprozil of the formula

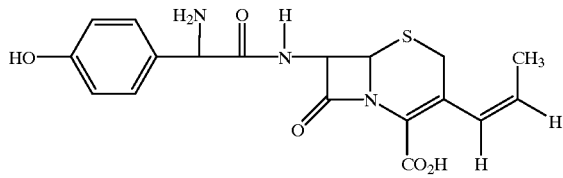

comprising the steps of
i) reacting a mixture of (Z)- and (E)-isomers of the compound of formula

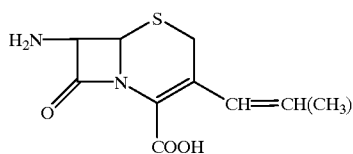

with hydrochloric acid, a lithium, sodium or potassium base, ammonia, or an amine of formula IV to form a salt of formula I

wherein $R_1$, $R_2$ and $R_3$ are independently hydrogen, $(C_{1-8})$alkyl, benzyl, $(C_{4-8})$cycloalkyl; or $R_1$ with $R_2$ and the nitrogen atom together is a 5- or 6-membered heterocycle which may contain one or two additional heteroatoms and $R_3$ is as defined above, wherein one of $R_1$, $R_2$, and $R_3$ is other than hydrogen; in a solvent or solvent mixture in which the Z- and E-isomers of said salt of formula I have different solubilities and where the E isomer is better soluble than the Z isomer and if desired, isolating a (Z)-isomer enriched 7-amino-3-(1-propen-1-yl)-3-cephem-4-carboxylic acid in free acid or salt form obtained by recovering said salt of (Z)-isomer enriched 7-amino-3-(1-propen-1-yl)-3-cephem-4-carboxylic acid after precipitation and where required, converting the enriched (Z)-isomer of the salt of formula I into the free acid of formula I ; and ii) further acylating said Z-isomer enriched 7-amino-3-(1-propen-1-yl)-3-cephem-4-carboxylic acid in free acid or salt form at the amine group in position 7 to obtain cefprozil in free form, in the form of a solvate, such as a hydrate or a hemihydrate, or in the form of a salt.

* * * * *